United States Patent [19]
Patrini et al.

[11] Patent Number: 5,159,121
[45] Date of Patent: Oct. 27, 1992

[54] CATALYST SYSTEM AND PROCESS FOR THE SELECTIVE PRODUCTION OF ISOPRENYL-ALKYLETHERS FROM ISOPRENE

[75] Inventors: Renata Patrini; Mario Marchionna; Massimo Lami; Francesco Ancillotti, all of Milan, Italy

[73] Assignee: Snamprogetti S.p.A., Milan, Italy

[21] Appl. No.: 824,943

[22] Filed: Jan. 24, 1992

Related U.S. Application Data

[62] Division of Ser. No. 676,361, Mar. 28, 1991, Pat. No. 5,120,868.

[30] Foreign Application Priority Data

Apr. 2, 1990 [IT] Italy .................. 19916 A/90

[51] Int. Cl.$^5$ .............................................. C07C 41/06
[52] U.S. Cl. ...................................................... 568/690
[58] Field of Search ........................................ 568/690

[56] References Cited

U.S. PATENT DOCUMENTS 4,146,738  3/1976  Jadamus et al. ................ 568/690

Primary Examiner—Howard T. Mars
Attorney, Agent, or Firm—Oblon, Spivak, McClelland, Maier & Neustadt

[57] ABSTRACT

A catalyst system for the selective production of isoprenylalkylethers from isoprene is described, characterized by satisfying the following empirical formula $$PdL_xL'_y$$

where L is a phosphorated binder in the form of an organic derivative of trivalent phosphorous of type $R_3P$ or $R_2P[CH(R)]_zPR_2$, in which the substituents R, which can be identical or different, are either hydrogen atoms or alkyl, cycloalkyl, aryl, alkoxy, aryloxy, arylthio or arylalkyl groups, and in which z is a whole number between 1 and 5;

L' is an easily displaceable binder chosen from dienes, olefins, anhydrides, diketones and nitriles;

x is a whole number between 0 and 4 and y is a whole number between 0 and 3, in which system excess phosphorated compounds of $R_3P$ or $R_2P[CH(R)]_zPR_2$ type may or may not be present.

8 Claims, No Drawings

CATALYST SYSTEM AND PROCESS FOR THE SELECTIVE PRODUCTION OF ISOPRENYL-ALKYLETHERS FROM ISOPRENE

This is a division of application Ser. No. 07/676,361, filed on Mar. 28, 1991 now U.S. Pat. No. 5,120,868.

This invention relates to a catalyst system and its use in the selective production of isoprenyl-alkylethers by etherification of isoprene with methanol or other alcohols under homogeneous liquid phase catalysis with transition metal complexes.

Acid-catalyzed decomposition of ethers such as 3-methyl-3-methoxy-1-butene, 3-methyl-1-methoxy-2-butene or 1,3-dimethoxy-3-methylbutane is a known path for producing isoprene [DE 2,213,701 (1972), J. O. Turner, Sun Res. and Dev. Co.].

It is also known to prepare said ethers by reacting isobutene with methylal [U.S. Pat. No. 3,758,610 (1973)—J. O. Turner Sun Oil Co.].

By combining the two processes in one or more stages, a monomer such as isobutene can be converted into monomer such as isoprene.

It is further known to prepare the aforesaid ethers by acid-catalyzed addition of an alcohol such as methanol to isoprene [U.S. Pat. No. 2,922,822 (1960)—L. K. Beach, N. J. Westfield—Esso].

Combining this reaction with subsequent separation and decomposition of the ethers would seem to be an interesting procedure for removing and recovering isoprene from hydrocarbon cuts which contain it in relatively large quantity, such as the $C_5$ fraction from steam cracking, and in this sense it could constitute a valid alternative to the conventional extractive distillation procedure.

However such $C_5$ fractions contain not only isoprene but also considerable quantities of 2-methyl-1-butene and 2-methyl-2-butene which as in the case of isoprene add methanol under acid catalysis, but give 2-methoxy-2-methylbutane as the product, this being known commercially as TAME.

It is apparent that if a $C_5$ fraction from steam cracking is subjected to acid-catalyzed etherification a mixture of TAME and isoprenyl ethers would be obtained, this being difficult to separate, as is clear from their boiling points:

| | | |
|---|---|---|
| 3-methyl-3-methoxy-1-butene | B.P. (°C.) | 83 |
| TAME | " | 86 |
| 3-methyl-1-methoxy-2-butene | " | 104 |

It is also known that as in the case of isoprenyl ethers, TAME decomposes to give the starting olefins 2-methyl-1-butene and 2-methyl-2-butene [FR 1,256,388 (1960)—Sinclair Res. Co.].

On decomposing the overall ether mixture a mixture of 2-methyl-1-butene and 2-methyl-2-butene would therefore be obtained, from which it would be difficult to isolate isoprene with sufficient purity because of the closeness of their boiling points, as is apparent from the following table:

| | | |
|---|---|---|
| 2-methyl-1-butene | B.P. (°C.) | 31 |
| isoprene | " | 34 |
| 2-methyl-2-butene | " | 39 |

It is further known that alcohols can be added to conjugate dienes in the presence of salts or complexes of transition or post-transition metals.

The first catalysts of this type investigated were those based on $RhCl_3.3H_2O$, with sufficiently selective formation of alkenyl-alkyl ethers [K. C. Dewhirst, J. Org. Chem. 32, (1967), 1297]. Later however the importance of acidity in this type of system was observed [B. W. Taylor, Amer. Chem. Soc., Div. Petrochem. Prepr., 17 (2). (1972), B141].

In fact these catalysts also etherify simple olefins because of their acid component, and cannot be used for selective etherification of 1,3-dienes in the presence of an olefin stream. At the beginning of the 1970s the main interest of researches was in directing the reaction of 1,3-dienes with alcohols towards the production primarily of dimerization or telomerization products. In this respect, if the reaction is conducted selectively on isoprene as a conjugate diene, terpene compounds could be obtained.

Reactions of this type have been studied mainly with catalysts based on complexes of Group VIII transition metals such as nickel and palladium [J. Tsuji, Adv. Organomet. Chem., 17 (1979) 141].

This reaction is catalyzed for example by Pd (0) complexes such as $Pd(PPh_3)_4$ [DE 2,635,250 (1978), H. Jadamus, K. Diebel, Chemische Werke Huels A. G.], and by phosphorated complexes of Pd (II) in the presence or absence of bases [JP 75/154 201, (1975)—K. Sawatari, E. Tanaka—Yoshitomi Pharmaceutical Industries Ltd.].

However, the dimerization or telomerization products are not suitable substrates for the production of isoprene by decomposition.

Only recently has it been sought to direct this type of catalysis towards the selective production of alkenyl-alkylethers, and thus reducing all those processes which lead to chain elongation and hence to the formation of dimers and/or telomers.

East German researchers have found that under suitable conditions the catalyst system consisting of palladium (II) complexes, phosphorated binders and bases such as sodium methoxide can selectively produce the desired ethers [DD 206,989 (1984)—H. Stegemann, H. Fuellbier, W. Gaube. E. Adler—VEB Chemisches Werk Militz].

This catalyst system suffers from various drawbacks.

The induction times are such as could cause reproducibility problems for the catalyst system.

The bases make the catalyst system less selective in ethers, as already observed in the literature [W. Gaube, H. Stegemann, J. Prakt. Chem., 326 (1984), 947].

In addition the presence of bases such as sodium methoxide can be harmful to the catalyst system, because it favours its reduction to palladium metal, which is inactive in this type of process. For the stated reasons, the selectivity of said system is not interesting from an industrial viewpoint.

The recently published U.S. Pat. No. 4,843,180 discloses a process directed towards the synthesis of unsaturated ethers, in presence of a catalyst based on nickel (0) and phosphines as chelants, process which provides high conversions with average reaction times (from 5 to 22 hours), using butadiene as starting diene. If using an hydrocarbon having a C number higher than 4 as starting diene, the same process presents a considerable reduction of the conversion. A new catalytic system has now been surprisingly found, which possesses all the required characteristics for selectively etherifying isoprene in the presence of a C5 fraction from steam cracking. This new system provides high conversions with, on average, low reaction times (from 1 to 6 hours). The new catalyst system comprises catalysts based on Pd (0) complexes with phosphorated binders in the presence or absence of excess phosphorated compounds.

Palladium (0) complexes have been hitherto known to favour only telomerization reactions.

With this catalyst system there are no induction times, characteristic of the system formed from palladium (II) complexes in the presence of phosphorated binders.

This new catalytic system also differs by having very high activity and selectivity in the production of isoprenyl-alkylethers and of leaving all olefins completely unaltered, including those having a double bond in the tertiary position.

This characteristic is not sufficiently available either with rhodium catalysts (which are not selective in the presence of simple olefins) or with the Pd (0) telomerization catalyst complexes, which are unable to produce alkenyl-alkylethers with the monomer alkenyl group.

The catalyst system of the present invention for producing isoprenyl-alkylethers from isoprene (such as contained in C5 hydrocarbon cuts) is characterised by satisfying the following empirical formula

PdLxL'y where L is a phosphorated binder in the form of an organic derivative of trivalent phosphorus of type $R_3P$ or $R_2P[CH(R)]_zPR_2$, in which the substituents R, which can be identical or different, are ether hydrogen atoms or alkyl, cycloalkyl, aryl, alkoxy, aryloxy, arylthio or arylalkyl groups containing preferably between 1 and 10 carbon atoms, and in which z is a whole number between 1 and 5; L' is an easily displaceable binder chosen from dienes (in particular butadiene, isoprene and 1,5-cyclooctadiene), olefins (in particular ethylene), anhydrides (in particular maleic anhydride), diketones (in particular dibenzylideneacetone [dba]), and nitriles (in particular acetonitrile and benzonitrile); x is a whole number between 0 and 4 and y is a whole number between 0 and 3, the sum of x+y being greater than or equal to 2. The aryl groups of part of the substituents R can also be substituted at the ring by other halogen or alkoxy groups.

The phosphorated binder L of $R_3P$ type is chosen preferably from trialkylphosphines such as tri-n-butyl-phosphine or triethylphosphine, and alkyl-aryl phosphines such as di-n-butylphenylphosphine. The phosphorate binder L of $R_2P[CH(R)]_zPR_2$ type is chosen preferably from those in which z is 4, such as 1,4-bis(-diphenyl-phosphino)butane (DPPB).

As above mentioned the catalytic system of the present invention can comprise excess phosphorated compounds of $R_3P$ or $R_2P[CH(R)]_zPR_2$ types, wherein the substituents R, which can be identical or different, are the same groups above mentioned for the binder L. The said excess phosphorated compounds are chosen preferably from tri-n-butyl-phosphine, triethylphosphine, di-n-butylphenylphosphine and 1,4-bis(diphenyl-phosphino)butane (DPPB).

The aforesaid palladium complexes with phosphorated binders can be prepared by the methods already exhaustively described in the literature [such as the preparation of Pd(Pn—Bu3)4 and Pd(PPh3)4 (where Bu=butyl and Ph=phenyl) is described by W. Kutan, A. Musco, in Inorg. Chem. Acta 12 (1975), 183, and by D. R. Coulson in Inorg. Synth. 13 (1972), 120].

The present invention further provides a process for producing isoprenyl-alkylethers from alcohols and isoprene present in a C5 stream from which cyclopentadiene has been removed preferably by thermal dimerization and most of the linear dienes (piperylene) have been removed preferably by fractional distillation.

The selectivity of the reaction towards isoprene rather than towards piperylene is further increased in the etherification reaction because the catalyst system when operating under the indicated preferred conditions selectively etherifies the isoprene.

Said process consists of reacting the C5 fraction obtained in this manner with alcohols in the presence of the aforedescribed catalyst system.

The alcohol is chosen preferably from $C_1$-$C_{10}$ alcohols and more preferably from methanol and ethanol.

The catalyst system operates in the absence of additional solvent as the C5 fraction is in itself a good solvent.

However additional solvents can if necessary be used. These can consist for example of non-conjugate olefinic substrates, paraffins, aromatic hydrocarbons, heavier alcohols such as isopropanol, or ethers, as can the reaction products themselves. If operating with one or more solvents, the concentration of the catalyst system can vary preferably between 0.0001 and 1 and more preferably between 0.001 and 0.1 molar for the palladium (0) complex and between 0 and 10 and more preferably between 0 and 1 molar for the added C5 phosphorated binder.

The isoprene/Pd molar ratio can vary preferably between 10 and 1000 and more preferably between 50 and 500, whereas the alcohol/isoprene molar ratio can vary preferably between 1 and 100 and more preferably between 5 and 50.

The reaction temperature is preferably less than 150° C. and more preferably between 50° and 130° C.

The operating pressure can vary between 0.1 MPa and 10 MPa, but more preferably is represented by the vapour pressure of the components of the reaction mixture.

When operating under the indicated preferred conditions, isoprene conversions exceeding 90% have been obtained, with initial rates of about 0.1 $s^{-1}$ (moles of isoprene converted per mole of palladium per second), and a very high isoprenyl-alkylether selectivity (between 80 and 100%).

The by-products obtained are generally dimers and a minimum of trimers, isoprene or telomers of the diene obtained by addition of the alcohol to the dimers.

The following examples are given to better illustrate the invention, but without representing a limitation thereon. (In the examples the stated percentages are molar).

EXAMPLE 1

This example illustrates the use of the catalyst of the present invention in reacting a C5 stream with methanol at 110° C. in a batch reactor.

0.27 mmoles of Pd(Pn—Bu3)4, 2.19 mmoles of Pn—Bu3, 820 mmoles of methanol and 144.3 mmoles of a C5 hydrocarbon mixture are mixed in a 100 ml autoclave with a magnetic stirrer. The C5 hydrocarbon mixture has the following composition: inerts 54.7%; isoamylenes 11.7%; isoprene 32.4%; piperylene (trans+cis)

0.5%; cyclopentadiene 0.7%. This feedstock was obtained from a further feedstock originating from steam cracking after thermal treatment to eliminate the cyclopentadiene and fractional distillation to eliminate the linear dienes.

A typical composition of feedstock from steam cracking is as follows: inerts 35.0%; isoamylenes 6.3%; isoprene 18.7%; piperylene 16.3%; cyclopentadiene 23.3%; benzene 0.4%. The inerts consist of saturated hydrocarbons and a mixture of linear pentenes and cyclopentene.

The operation is carried out under a nitrogen atmosphere, heating to 110° C.

Operating in this manner an isoprene conversion of 97% was obtained after 3 hours, with an isoprenyl-methylethers selectivity of 86% (yield 83%), a piperylene conversion of 87% with a pentenyl-methylethers selectivity of 98% (yield 85%), and a cyclopentadiene conversion of 57% with a cyclopentenyl-methylethers selectivity of 8% (yield 4%, the remainder being dicyclopentadiene).

None of the other mixture components (including the isoamylenes) undergo any reaction.

The isoprenyl ethers selectivity within the $C_5$ ether fraction exceeds 98%.

EXAMPLE 2

This example shows how the selectivity of the catalyst system for isopropene compared with piperylene and cyclopentadiene can be increased by altering the experimental conditions.

The procedure is carried out under the same conditions as in Example 1 but using a temperature of 100° C.

Operating in this manner an isoprene conversion of 40% was obtained after 6 hours, with an isoprenyl-methylethers selectivity of 89% (yield 36%), a piperylene (cis+trans) conversion of 8% with a pentenyl-methylether selectivity of 99% (yield 8%), and a cyclopentadiene conversion of 15% with a cyclopentenyl-methylethers selectivity of 18% (yield 3%).

Again, none of the other mixture components undergo any reaction. The isoprenyl ethers selectivity within the $C_5$ ether fraction exceeds 99%.

EXAMPLE 3

This example shows how selective etherification of isoprene can be conducted in the presence of an added solvent.

The procedure of Example 1 is followed, but feeding the autoclave with 0.137 mmoles of $Pd(Pn-Bu_3)_4$, 1.096 mmoles of $Pn-Bu_3$, 20.6 mmoles of isoprene, 411 mmoles of methanol and 40 ml of anhydrous toluene as the added solvent.

Operating in this manner an isoprene conversion of 72% was obtained after one hour of reaction, with a methyl-isoprenyl ethers selectivity of 89% and yield of 64%.

EXAMPLE 4

This example shows how an active and selective catalyst system is still obtained under mild conditions.

The conditions of Example 3 are followed, but using a temperature of 80° C. and 0.18 mmoles of tri-n-butyl-phosphine.

A conversion of 74% was obtained after one hour of reaction, with a methyl-isoprenyl ethers selectivity of 90% and yield of 67%.

EXAMPLE 5

This example shows that the catalyst system also gives high performance with other phosphines of $R_3P$ type.

The conditions of Example 3 are followed, but the catalyst system consists of $Pd(Pn-Bu_2Ph)_4$ (0.137 mmoles) in the presence of 1.10 mmoles of $Pn-Bu_2Ph$.

A conversion of 83% was obtained after 6 hours of reaction, with a methyl-isoprenyl ethers selectivity of 85% and yield of 71%.

EXAMPLE 6

This example shows that good performance of the catalyst system is also obtained with other phosphines of $R_2P[CH(R)]_2PR_2$ type. The conditions of Example 3 are followed but with a temperature of 60° C. and a catalyst system consisting of $Pd(DPPB)_2$ (0.137 mmoles) in the presence of 0.55 mmoles of DPPB.

A conversion of 12% was obtained after 6 hours of reaction, with a methyl-isoprenyl ethers selectivity of 85% and yield of 10%.

EXAMPLE 7

This example shows that moderate performance of the catalyst system is obtained with a complex of the $PdL_xL'_y$ type (where $x=0$, $y=2$), such as $Pd(dba)_2$.

The conditions of Example 3 are followed but with a temperature of 100° C. and a catalyst system consisting of $Pd(dba)_2$ (0.137 mmoles) in the presence of 1.65 mmoles of $nBu_3P$.

A conversion of 5% was obtained after 3 hours of reaction, with a methyl-isoprenyl ethers selectivity of 85% and yield of 4%.

EXAMPLE 8 (Comparative)

This example shows that in our invention the yields of desired products are maximized for equal experimental conditions, compared with that claimed previously in the literature.

The method and experimental conditions described in Example 4 are followed.

The catalyst system is prepared as described in the patent DD 206,989, and consists of 0.07 mmoles of $[Pd(C_3H_5)Cl]_2$, 0.82 mmoles of $PnBu_3$ and 0.21 mmoles of $CH_3ONa$.

After one hour of reaction an isoprene conversion of 57% was obtained with a methyl-isoprenyl-ethers selectivity of 65% and a yield of 37%.

EXAMPLE 9 (Comparative)

This example shows that in our invention the yields of desired products are maximized for equal experimental conditions, compared with that previously described in the literature, even if other phosphorated binders are present.

The conditions described in Example 5 are followed.

The catalyst system is prepared as described in the patent DD 206,989, and consists of 0.07 mmoles of $[Pd(C_3H_5)Cl]_2$, 1.64 mmoles of $Pn-Bu_2Ph$ and 0.21 mmoles of $CH_3ONa$.

After 6 hours of reaction an isoprene conversion of 83% was obtained with a methyl-isoprenyl ethers selectivity of 72% and yield of 60%.

EXAMPLE 10 (Comparative)

This example shows that it is not possible to conduct selective etherification of isoprene in the presence of an olefinic stream using a rhodium catalyst system [see K. C. Dewhirst, J. Org. Chem. 32, (1967), 1297].

The procedure of Example 1 is followed. 0.57 mmoles of $RhCl_3 \cdot 3H_2O$, 14.7 mmoles of isoprene, 14.7 mmoles of 2-methyl-1-butene and 750 mmoles of methanol are however fed into the autoclave at 60° C.

After 6 hours the isoprene conversion was 87%, with a methylisoprenyl ethers selectivity of 89% (yield 77%).

A part of the 2-methyl-1-butene isomerizes to 2-methyl-2-butene, which is also converted to TAME.

The TAME yield from both isoamylenes is 51%.

We claim:

1. A process for the selective production of isoprenyl-alkylethers from isoprene present in a $C_5$ stream from which the cyclopentadiene and most of the linear dienes (piperylene) have been removed which comprises: reacting the $C_5$ fraction obtained in said manner with alcohols in the presence of a catalyst system satisfying the following empirical formula $$PdL_xL'_y$$

where L is a phosphorated binder in the form of an organic derivative of trivalent phosphorus of type $R_3P$ or $R_2P[CH(R)]_zPR_2$, in which the substituents R, which can be identical or different, are either hydrogen atoms or alkyl, cycloalkyl, aryl, alkoxy, aryloxy, arylthio or arylalkyl groups, and in which z is a whole number between 1 and 5; L' is an easily displaceable binder chosen from dienes, olefins, anhydrides, diketones and nitriles; x is a whole number between 0 and 4 and y is a whole number between 0 and 3, the sum of $x+y$ being greater than or equal to 2.

2. A process as claimed in claim 1, wherein excess phosphorated compounds of $R_3P$ or $R_2P[CH(R)]_zPR_2$ type are present.

3. A process as claimed in claim 1, wherein the isoprene/Pd molar ratio varies between 10 and 1000 and the alcohol/isoprene molar ratio varies between 1 and 100.

4. A process as claimed in claim 3, wherein the isoprene/Pd molar ratio varies between 50 and 500 and the alcohol/isoprene molar ratio varies between 5 and 50.

5. A process as claimed in claim 1 and possibly 2, wherein the catalyst system operates in the presence of one or more added solvents, with a molar concentration of between 0.0001 and 1 for the palladium complex ($PdL_xL'_y$) and between 0 and 10 for the excess added phosphorated compound.

6. A process as claimed in claim 5, wherein the molar concentration of the palladium complex is between 0.001 and 0.1 and for the excess added phosphorated compound is between 0 and 1.

7. A process as claimed in claim 1, wherein the reaction is conducted at a temperature of less than 150° C. and at a pressure of between 0.1 and 10 MPa.

8. A process as claimed in claim 7, wherein the temperature is between 50° and 130° C.

* * * * *